(12) United States Patent
Shaw et al.

(10) Patent No.: US 6,803,215 B1
(45) Date of Patent: Oct. 12, 2004

(54) SEQUENCE CHARACTERIZED AMPLIFIED REGION (SCAR) TEST FOR THE AUTHENTICATION OF TRADITIONAL CHINESE MEDICINAL MATERIALS

(75) Inventors: Pang-Chui Shaw, Shatin (CN); Jun Wang, Shatin (CN); Paul Pui-Hay But, Tai Po (CN); Wai-Yan Ha, Kwun Tong (CN); Forrest C. F. Yau, Lam Tin (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 09/706,228

(22) Filed: Nov. 3, 2000

(51) Int. Cl.[7] .......................... C12P 19/34; C12Q 1/68; C07H 21/04

(52) U.S. Cl. ..................... 435/91.2; 435/91.1; 435/6; 536/23.1; 536/24.3; 536/24.33; 536/25.32

(58) Field of Search ............................... 435/91.2, 91.1, 435/6; 536/24.33, 23.1, 24.3, 25.32, 22.1, 25.4

(56) References Cited

U.S. PATENT DOCUMENTS

| | | | |
|---|---|---|---|
| 5,747,538 A | | 5/1998 | Meybeck et al. |
| 5,861,244 A | * | 1/1999 | Wang et al. .................... 435/6 |
| 5,876,977 A | * | 3/1999 | Wang et al. ................ 435/91.2 |
| 5,965,697 A | * | 10/1999 | Czaplewski et al. ......... 530/324 |
| 6,309,840 B1 | * | 10/2001 | Wang et al. .................... 435/6 |

FOREIGN PATENT DOCUMENTS

EP        0644 267 A2  *  3/1995

OTHER PUBLICATIONS

Desmarais et al., "Direct amplification of length polymorphisms (DALP),or how to get characterize new genetic markers in many species"; *Nucleic Acids Research* (1998), pp. 1458–1465, vol. 26, No. 6.
Myburg et al., "Development of RAPD and SCAR markers linked to the Russian wheat aphid resistance gene Dn2 in wheat," *Theor Appl. Genet.* (1998), pp. 1162–1169, vol. 96.
Savelkoul et al., "Amplified–Fragment Length Polymorphism Analysis: the State of an Art," *Journal of Clinical Microbiology* (1999), pp. 3083–3091, vol. 37, No. 10.
Shaw et al , "Authentication of Panax Species and their Adulterants by Random–Primed Polymerase Chain Reaction," *Planta Med.* (1995), pp. 466–469, vol. 61.
Zhang et al., "Random Primed Polymerase Chain Reaction Differentiates *Codonopsis pilosula* from Different Localities," *Planta Medica* (1999), pp. 157–160, vol. 65.

* cited by examiner

*Primary Examiner*—Kenneth R. Horlick
*Assistant Examiner*—Cynthia Wilder
(74) *Attorney, Agent, or Firm*—Townsend and Townsend and Crew LLP

(57) ABSTRACT

Methods are provided for the authentication of traditional ingredients in Chinese medical materials. Arbitrarily primed polymerase chain reaction techniques are employed to identify genomic regions that are polymorphic between ginseng species of the genus Panax and between snake species of the family Serpentiformes. The sequence of these polymorphic regions is used to design specific primers that will amplify a unique region from the species of interest. These sequence characterized amplified regions (SCAR) may be used to rapidly amplify a diagnostic nucleic acid from herbal and medicinal materials. The present invention therefore provides rapid and sensitive methods for identifying ingredients in traditional Chinese medicines, and distinguishing them from common adulterants or ersatz ingredients.

16 Claims, 14 Drawing Sheets

Fig. 2.

```
                                          (SCAR.F2)
RAPDAG                            TTCGCCACCC GGAGCAGCAT TGAGATCCGC
                     10         20         30         40         50
           (SCAR.F1)
RAPDAG   1 CAAGTCAACT GCAGGGGTTA AGAAGCCCTT AAAAATCCAG TGAAGTTTCC   50
WAG      1 ********** ********** ********** ********** **********   50
CAG      1 ********** ********** ********** ****-***** **********   49
DG       1 ********** ********** ********** ********** **********   50
HG       1 ********** ********** ********** ********** *****C****   50

60         70         80         90        100
RAPDAG  51 TTGGTCTGCT TCATTGCTTC TCAATTCGAT CATCGGTGTG AGCTCGTCAA  100
WAG     51 *A** ****** ****** ****** ********  100
CAG     50 *A** ****** ****** ****** ********   99
DG      51 *A** *A ******G* ******** ********  100
HG      51 *A** *A ******G* ******** ********  100

110        120        130        140        150
RAPDAG 101 CCTTTTGTCA GTCAAAGTCC TCACCCACTC CTGCCCATTG AAAATT       150
WAG    101 ********** ********** ********** ********** **********  150
OAG    100 ********** ********** ********** ********** **********  149
DG     101 ********T* ******** ******** *CA* ****----  146
HG     101 ********T* ******** ******** *CA* ****----  146

160        170        180        190        200
RAPDAG 151                              TTGCCAACT T-ATTTAATA CACTTCTCCT  199
WAG    151 ********** ********** ********** *C******** **********  200
OAG    150 ********** ********** ********** *C******** **********  199
DG     147 ---------- ---------- -********* *C******** **********  175
HG     147 ---------- ---------- -********* *C******** **********  175

210        220        230        240        250
RAPDAG 200 TCCATTCGGC TATAAAGGCA GCTAAGCATA AGGATCAAAT ACACCAGCAA   249
WAG    201 ********** ********** ********** ********** **********  250
OAG    200 ********** ********** ********** ********** **********  249
DG     175 ********** ********** ********** ********** **********  224
HG     175 ********** ********** ********** ********** **********  224

260        270        280        290        300
RAPDAG 250 CAATACGTAC TCCCATCCTA GAGAGGAAAA GAGAAAGGGA GAGAAAAGCT   299
WAG    251 ********** ********G* ********** *****-**** **********  299
OAG    250 ********** ********G* ********** *****-**** **********  298
DG     225 ******A*** ********G* ********** ********** **********  274
HG     225 ******A*** ********G* ********** ********** **********  274

310        320        330        340        350
                                         (SCAR.R1)
RAPDAG 300 TTTGTAAAGC TTTAGAAAAA TAGAGAGAGA AAGATAGTTC AAATAAAA-G   348
WAG    300 ********** ********** ********** ********** *******A*   349
OAG    299 ********** ********** ********** ********** *******A*   348
DG     275 ********** ********** ********** ********** *******G*   324
HG     275 ********** ********** ********** ********** *******G*   324

360        370        380        390
                               (SCAR.R2)
RAPDAG 349 GGTGTTTTAT TTGGGTTCCA TCACATAGTT ATTGTGGCGA A            389
WAG    350 *......... .......... .......... .......... .            350
OAG    349 *......... .......... .......... .......... .            349
DG         .......... .......... .......... .......... .
HG         .......... .......... .......... .......... .
```

Fig. 3.
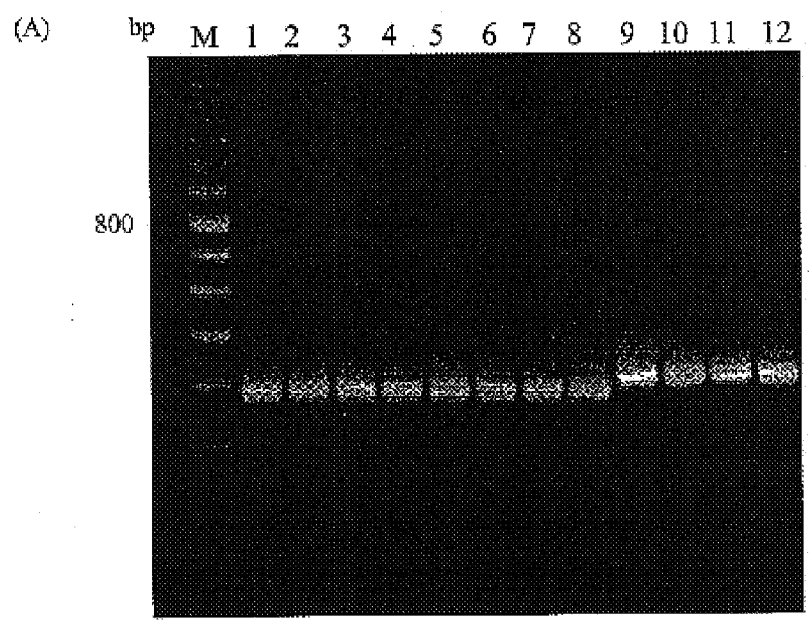
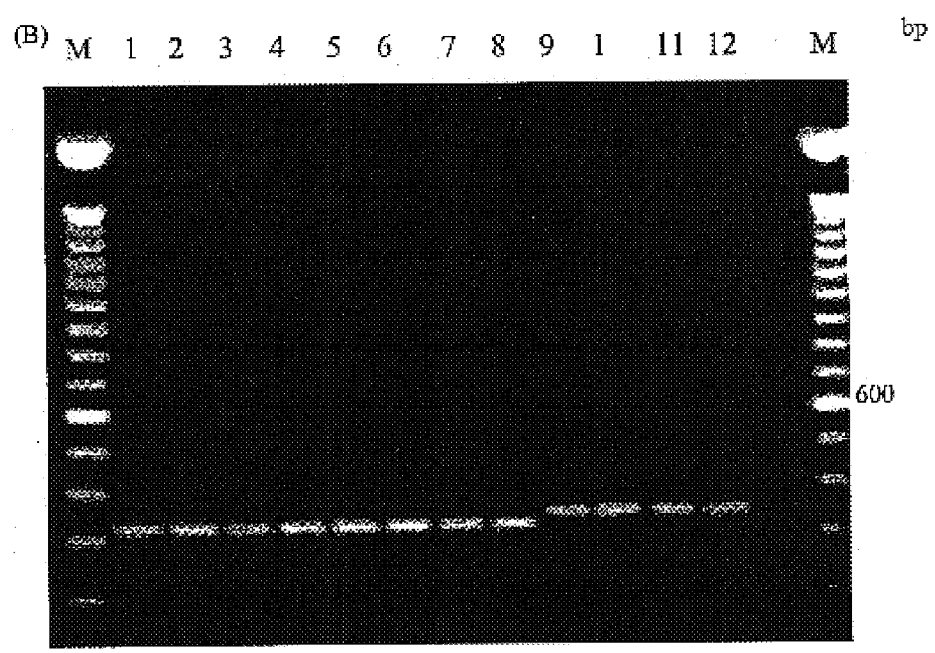

Fig. 6.

```
        (C2S8.4F)10        20         30         40         50         60
     5' GTGAGGCGTC TAAACAAAAA CGAAGAAGCA GAAAGCACAG AACCAGAGAC CAAAGAAGAA
               70         80         90        100        110        120
        GAAAAGAAGA AAAAAAGAAA AAGCAGAGAA CGAAAAAAAA GAAAGAAAAG AAAGCAGCGT
              130        140        150        160        170        180
        CGCGACTCGC GACTAGAGAA GAAAGAAGAA CATACTAGCA AAGAAGAAGC AATCGGAGCT
              190        200        210        220        230        240
        AGGGGTAGTC GTCATTGGTC AGAGTTCCAG TATTCAACCA CTCACCAGTC TCTCTCTCCC
              250        260        270        280        290        300
        AAATCTCCCC TTTCTACTCT TCTACTGTAA ATCGCGATTA GGGCCAATTA TCTCTTCTCG
              310        320        330        340        350        360
        GAACGACGTC GTTTTTTTTT AAACCGGTTC TCCATTGGGT CAATCCATAC CCATAGCAAA
              370        380        390        400        410        420
        TCCAAATCGC TCTCTCAGCT CGTCTAAGTA GTCGACGAGG CGCCCATGGC GACGACTTGC
              430        440        450        460        470        480
        TTTCCCAGGC ACTCGACTTG CAGACCTCCA CCAAGTCGGC CAACCGCCTT CTTCTTCGGA
              490        500        510        520        530        540
        TCGACTGGAC GTCTAGTCGA CGCATTAACA ACTATGACAC AAACTAAGGC TTTTACAATT
              550        560       570(C2S8.4R)580        590        600
        AGAGATGATC AAAGACCATT CTTACTTGAC GCCTCAC 3'
```

Fig. 8.

```
(DALP1.7F3) 10         20         30         40         50         60
5' CGCTCCCACT GACCCTTTTG TACACACTAG GTTCATTCTT ATTGCTGATA AAATCAAACT
            70         80         90        100        110        120
   CTTTTGATTT ATTTCATCAA AGCGAATGTT CCATTTTTGA GAAGCTTGCT TCAGTCCATT
           130        140        150        160        170        180
   CCTCTGAGTG TCTACAACTC TTACCTCATG TAACTGGATC ATCATCTTCT GTGATGTGTA
           190        200        210        220        230        240
   CCTCATCATC ATCATCATCT ATAATGAATC CATACCTCCT AGGTATCGT CGGTATTATTC
           250        260        270        280        290        300
   TAGATTTACG ATTCGGTTGT GGTGCAATAG GTCTATCTAC AGGTTCCTCT TATTTGACTT
           310        320        330        340        350        360
   ATAGTGTTTT GTGGTTCTTG AACTCTTCAA GATCTATTAT CCTCCCACTA GCCCCTTTAA
           370        380        390        400        410        420
   TGATAAACAC CTTTATCTTA GAAGGTAGTG TGTTTCACAA TAAACACCTT TTGCTAAGTA
           430        440        450        460        470        480
   GGATTATAGA GACATTGAGG TCAGCCACGT ATTGCCACAC CCATTCTGTA GGGGTATTTA
           490        500        510        520        530        540
   CGAGCAGTTT GGTCTTGCTG TATGTGTGGT TCATGTCACA CTTGAGACTG ATTGGCATAT
           550        560        570        580        590        600
   TCTGACGTCA TGGGTACTAT TTTTCCCATG AGATAGCCAT GTCTTACTCT TTTCAGCCAG
           610        620        630 (DALP1.7R3)
   CGTAGTGTAC AGATGTTGCA TCATGGTCAT AGCTGT 3'
```

Fig. 11

```
           10         20(SCAR-Af)30         40         50
5' TGCTGCAGGT CCTGTCAGCC TGATTATTCA AGTTGGTGAG GTCCAAGATG
           60         70         80         90        100
   AGGGTCTTTT CTGCTCTTAC CCTCTGGACC ATCTTGCTCC CCAATGTAAG
          110        120        130        140        150
   GTTGCCCCAA CCCTCCTGTC TTTTCGTAAG GGCCTGAAGA CGTGGCTTTG
          160        170        180        190        200
   CAATGCAAAT CAAACAAAAC ACCACCATTT GGGGCCCCAG TGAATGAACA
          210        220        230        240        250
   GCACAATAGA GGTGGTTGAT AGAGTCATAA CAGATCCCAC CTGCCCTCCA
          260        270        280        290        300
   ATCCACCCCC CAACCTCCCC ATGTGTCTTT GATTGTAAGG TTTGATTTTA
          310        320        330        340        350
   ACATTTGTG TTTTAACTAA GATGTAACTA TAAGCCGCAG AGAGTTACTC
          360        370        380        390        400
   TATGGTAAGA TGCAGGGCCA ATAAATTTGA TAAATAAACA AATCAAATCA
          410        420        430        440        450
   AATCAATTGT CACTGCCTTC TTACTGATA TGCCTGCTACA TCTAAGCTGC
          460(SCAR-Ar)470        480        490        500
   ATATTCTCC CTTCAAATTC ATTCCAAGT TCAAAAATATC TCCTACATTT
          510        520        530        540        550
   TCAAATCAAG CAGCAGCACC ATGAGGAGC AATCATCTTAT AATCAGTATT
          560
   CACCTGCAGC A 3'
```

Fig. 12.

```
              10         20         30         40         50
5' TGCTGCAGGT CCCATTAGTT AATGAGTAAC CTCCCGGGGC CCAAAAAGAG
              60         70         80         90        100
   AGTTTTCTCT GCCTTTACCC CGCTGCCCGC CGTGAAAACC TCCCCACTCT
             110        120        130        140        150
   CTTGGCCTTT CATAAAGGTG TTAAAAACAT GGCTCTGCAT CTTTTCTTGC
   (SCAR-Bf)160        170        180        190        200
   ACCAATGAAA GGGAAGGTTG GTGCCCTGAC AGCCTCCCAC CTTTTAATCA
             210        220        230        240        250
   ATTTGTTACA TTCCTTGCTT GTTTTAAATT TTACATACTT TTATATGCTT
             260        270        280        290        300
   TTAATACTTT ATTGTATTTG CTTGAATTG  CTTTGTGAAG GAGATGGAAG
             310        320        330        340        350
   GTTCTTAAAT ATGACAAACA ATAATTAGT  GAATTCAGGT GTGTTTTGCT
             360        370        380        390        400
   GTGTAGGGAA ATGGTATACT ATATGTTTAG TATATTGTAT CTTCCATGCA
             410        420       430(SCAR-Br)440         450
   TATCAGGTAT ACAGGTTGGA TCTGAGCAAA ACTGAGAGCA AATTGGAGAG
             460        470        480        490        500
   CAAATTCCCA TCTCTTCAAC TCCTTTAAAA ACACTCCGGA GATTAGGAAA
             510        520        530        540        550
   ACTTCATATG AAGAAGGATG TCAATAGAGA TCATATTTCT TTTTCCACTG
             560        570        580        590        600
   TTTTGTTTCT GAGAATGTCT CCTTGGATCA GAAAAGAAAA CTGTTGACCT
   GCAGCA
```

Fig. 13.

```
            10         20         30         40         50
5'  TGCTGCAGGT ATGATAGTTC CAAAAATTAC TAGCCTTCAA TTTCTAAACA
            60         70         80         90        100
    ACAAATTAAA TTCTGATTAC AATATACTAC TCAGTGATAT TGTTCATTAA
           110        120        130        140        150
    GAGGAATTCT ACATATTTAA CAATTGTATT CTAGTGCAAT TTGAAATAT
           160        170        180        190        200
    AAAAGCTCAA GCAAAACAGA TTAAGCCCCT TCAACTCGA AAAGGTCCCA
    (SCAR-Zf)210        220        230        240        250
    AGACAACTTA TAAGATCTAC CAGTGGTTTC AAAGTAAAAA AAAAACAAAA
           260        270        280        290        300
    ACTAAATAGG TTTTAGGATT TCACAAGTAA AAGGGTGACA ATAGAGCATA
           310        320        330        340        350
    CCACAGTTGT TTTTGGTATA ATTGTAGTTT TAATTGTCAA AGCAATTAAA
           360        370        380        390        400
    TGTAACTGGG CAGATGAAAG CTGAGTGGAC CAATAAGAAC AGATTGACTA
           410        420        430        440        450
    CACCTCTTAA TTAAGAAGGA AAGAATGTAC ATTTGTGAAT GTTGTTCACT
           460        470        480        490        500
    ATATATATAG AGAGAGAACA AATGAAAGGA TACGATATCA TCAAGGGAGT
           510        520(SCAR-Zr)530        540        550
    TAAAGAATTG AAACGGGAAA TGGACTAGCA AGAAGAACTG ATGGTAGGTG
           560        570        580        590        600
    GACCAAGGCA GCCATAGACT GGATCCCCCT TGATAATAAG TGGCCTTGAA
           610        620        630        640        650
    AGAGACCTAC AGTAAAACAA GACTGATCAA TAACATCAGC AAGTATTGCG
           660        670        680        690        700
    GGCCAAAAAA AGCTCAGGAC CATTGGAAAC ATGAGGAAGA GGCATCCTGC
           710        720        730        740        750
    AGTGGATAGA CAATGGCTAA GATGATGATG ATGATGATGA TGATGATGAT
           760        770        780        790        800
    GATGATGATG ATGCAGTCAA ATATCAGTAA ATGCAGTTGC TTCGATATAT
           810        820        830        840        850
    GGAGAGTAAC AAGCAAGCAA ATGTTGCTTT TGCTTTTGAC TTGCTGTGGC
           860        870        880        890        900
    ACAAACACTA AATCTAATGA CCATACATAT TGAAAGATGT TAGTTTGCTG
           910        920
    TATGAAATGA ACACTTTTGA CCTGCAGCA
```

SEQUENCE CHARACTERIZED AMPLIFIED REGION (SCAR) TEST FOR THE AUTHENTICATION OF TRADITIONAL CHINESE MEDICINAL MATERIALS

CROSS-REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable.

FIELD OF THE INVENTION

This invention is directed to the authentication of Chinese medicinal materials based upon analysis of nucleic acid polymorphisms in an amplified region characteristic of the material in question.

BACKGROUND OF THE INVENTION

Traditional Chinese medicine has been practiced by the Chinese people for 2–3 millennia. It also currently covers the practice and medicinal materials used by Tibetan, Mongolian and other ethnic minorities. This system with its materials has been spread and adopted by other Asian countries such as Japan, Korea and Vietnam.

Chinese medicinal materials have been recorded in various pharmacopoeia. One of the classical references Bencao Gangmu written by Li Shi Zhen in the late 14th Century contains about 2,500 items of herbs and other products (animals and minerals). The official pharmacopoeia of the People's Republic of China (1995 ed.) contains 2,375 items of medicinal materials. These medicinal materials are described by their organoleptic characteristics and it is not uncommon to have substitutes or even adulterants in the market. For examples, herbal preparations purporting to contain *Panax quinquefolius* (American ginseng) may actually contain the less expensive *P. ginseng* (Asian ginseng). Several poisonous herbs, e.g., *Phytolacca acinosa* Roxb, *Mirabilis jalapa* L., and *Talnium paniculatum*, have been found in medicinals purporting to contain *P. ginseng*. Similarly, less expensive snakes of different species or even families have been substituted for the three snake crude drugs in the pharmacopoeia, *Agkistrodon actus, Bungarus multicinctus multicinctus* and *Zaocys dhumnades*.

Also, in the market, many medicinal materials exist in powder or shredded slices, rendering their authentication by organoleptic approaches difficult. For the safety of consumers, more effective methods for identification are needed. The presence of these methods also helps the modernization of traditional Chinese medicine and safeguards the healthy development of the medicinal industry. Analytical techniques such as thin-layer chromatography (TLC), high-performance liquid chromatography (HPLC), and liquid chromatography/mass spectrometry (LC/MS) may be applied to identify the components in the sample (Lang et al., *J. Chi. Pharm. Sci.*, 2:133–43 (1993)). Nevertheless, the level of the components is easily affected by growing climates, harvesting period and storage conditions. Therefore, for accurate authentication, other independent approaches are needed.

Advances in molecular biology have offered a promising tool and sensitive alternative means for the authentication of medicinal materials. U.S. Pat. No. 5,876,977 discloses the use of polymerase chain reaction-restriction enzyme length polymorphism (PCR-RFLP) analysis to identify herbal materials. It involves first using PCR to amplify a specific region of the genome, and then the appropriate restriction enzyme to cleave the amplified DNA into defined fragments characteristic of the animal or plant medicinal material. However, PCR-RFLP suffers from several disadvantages. Amplification and restriction require two separate enzymatic steps. Moreover, PCR-RFLP depends on the identification of specific restriction site sequence polymorphisms that will yield unique digestion patterns for the particular restriction enzymes chosen.

The present invention employs Random Amplified Polymorphic DNA (RAPD) (Williams et al., *Nucleic Acids Res.* 18:6531–5 (1990)) and Direct Amplification of Length Polymorphism (DALP) (Desmarais et al., *Nucleic Acids Res.* 26:1458–65 (1998)) to generate DNA fragments polymorphic to the species under study. Both methods do not require prior genetic knowledge of the sample. In RAPD, a single primer of 10or more nucleotides is used to amplify the genomic DNA. Amplification is under less stringent conditions. In DALP, a pair of primers longer (usually 20–27 bp) than RAPD is used and amplification is performed under more stringent conditions. Both give rise to DNA fragments which produce fingerprints after separation by gel electrophoresis. The origin of these fragments is not defined but they presumably contain DNA sequences complementary to the 3' end of the primer sequence. Desirable RAPD or DALP polymorphic bands are converted to SCAR (Sequence Characterized Amplified Regions) by first sequencing the band and then designing specific primers for amplification of the specific bands under high stringency conditions.

SUMMARY OF THE INVENTION

In one aspect of the invention, an herbal material purporting to contain ginseng is identified by extracting nucleic acids from a sample of the herbal material, amplifying a polymorphic region of the nucleic acid with two or more oligonucleotide primers, resolving the amplification products, and comparing the pattern of amplification products with that from amplification of known herbal materials. In this way, an unknown herbal sample may be identified as *Panax ginseng, Panax quinquefolius, Panax notoginseng* (Burk), *Panax japonicus major, Panax japonicus, Panax trifolius, Mirabilis jalapa* L., or *Panax acinosa* Roxb, or whether the herbal material is from another source.

In another aspect of the invention, a medicinal material purporting to contain extract of a particular snake is identified by extracting nucleic acids from a sample of the medicinal material, amplifying a polymorphic region of the nucleic acid with two or more oligonucleotide primers, resolving the amplification products, and comparing the pattern of amplification products with that from amplification of known snake extracts.

An additional aspect of the invention provides isolated nucleic acids comprising polymorphic regions that may be amplified to identify unknown materials. Still another aspect of the invention provides sets of oligonucleotide primers that amplify polymorphic regions residing between them.

In an embodiment of the invention, the nucleic acid extracted from the herbal or medicinal material is genomic DNA. In an embodiment of the invention, the amplification products are resolved by gel electrophoresis and visualized by fluorescence.

In one embodiment of the invention, the apparent molecular weight of an amplification product from the unknown material is compared with the size of amplification products from known materials to identify the unknown material. In another embodiment, the unknown material is identified by the presence of an amplification product present in the known material, while in yet another embodiment the unknown material is identified by the absence of an amplification product absent from the known material.

In an embodiment of the invention, a polymorphic region of ginseng is first identified by RAPD, employing primer OPC-20. In one embodiment, the polymorphic region identified by DALP comprises a SCAR2 sequence amplified in both *P. quinquefolius* and *P. ginseng*, and differing in sequence between various isolates of these species. In a further embodiment, the SCAR2 region is amplified as a SCAR using the primer pair SCAR.F1 and SCAR.R1.

In an embodiment of the invention, a polymorphic region of ginseng is first identified by DALP, employing primers DALP001 and DALPR1. In one embodiment, the polymorphic region identified by DALP analysis comprises the sequence of DALP1.7, amplified only in *P. ginseng*. In a further embodiment, the DALP1.7 region is amplified as a SCAR using the primer pair DALP1.7F3 and DALP1.7R3.

In an embodiment of the invention, a polymorphic region of ginseng is first identified by RAPD, employing the primer OPC-02. In one embodiment, the polymorphic region identified by RAPD comprises the sequence of C2S8.4, amplified only in *P. quinquefolius*. In a further embodiment, the C2S8.4 region is amplified as a SCAR using the primer pair C2S8.4F and C2S8.4R.

In an embodiment of the invention, a region polymorphic among different snake species is first identified by RAPD, employing the primer OPF-14. In one embodiment, the region identified by RPD comprises a sequence amplified only in *A actus* and may be amplified as a SCAR using primer pair SCAR-Af and SCAR-Ar. In another embodiment the region identified by RAPD comprises a sequence amplified only in *B. multicinictus multicinctus* and may be amplified as a SCAR using primer pair SCAR-Bf and SCAR-Br. In yet another embodiment, the region identified by RAPD comprises a sequence amplified only in *Z. dhumnades* and may be amplified as a SCAR using primer pair SCAR-Zf and SCAR-Zr.

BRIEF DESCRIPTION OF THE DRAWINGS

FIG. 2. Sequence alignment of SCAR fragments generated using primers SCAR.F1 (SEQ ID NO:7) and SCAR.R1 (SEQ ID NO: 8) (underlined). RAPDAG (SEQ ID NO:2) is the original RAPD fragment amplified by primer OPC-20 (in bold) from *P. quinquefolius* from a farm in the USA (FIG. 1). Primers SCAR.F2 (SEQ ID NO:9) and SCAR.R2 (SEQ ID NO:10) are also underlined. WAG (SEQ ID NO:3) and AG (SEQ ID NO:4) are *P. quinquefolius* from Wisconsin and Ontario, respectively. DG (SEQ ID NO:5) and HG (SEQ ID NO:6) are *P. ginseng* from Xingbing of Liaolin province and Kangwon, respectively. The extra 25 bp in *P. quinquefolius* are shaded. Gaps are represented by a dash.

FIG. 3. SCAR analysis using primers (A) SCAR.F1 and SCAR.R1. (B) SCAR.F2 and SCAR.R2. Lanes 1 to 8 are *P. ginseng* from Ji'an county of Jilin province, Xingbing county of Liaolin province, Kangwon, Pochon, Kanghwa, Kumsan, Kimpo and Xinkiahe, respectively. Lanes 9 to 12 are *P. quinquefolius* from British Columbia, Ontario, Wisconsin and a farm in the USA, respectively. M is the 100 bp marker from (A) Pharmacia and (B) Gibco BRL, respectively.

FIG. 6. Sequence of the polymorphic band of *P. quinquefolius* generated by the OPC-02 primer. Total length of the fragment is 577 bp (SEQ ID NO: 12). RAPD primer sequences (OPC-02) are in bold. SCAR primer sequences (C2S8.4F (SEQ ID NO: 13) and C2S8.4R (SEQ ID NO: 14)) are underlined.

FIG. 8. Sequence of the polymorphic band of *P. ginseng* (SEQ ID NO:17). The sequence of the sample of Jilin province Ji'an County is identical to that of Kangwon. Total length of the fragment is 636 bp. DALP primer sequences (DALP001 and DALPR1) are in bold. Designed primers DALP1.7F3 (SEQ ID NO:18) and DALP1.7R3 (SEQ ID NO:19) for DALP analysis are underlined.

FIG. 11. Sequence of the SCAR fragment generated using primers SCAR-Af (SEQ ID NO:24) and SCAR-Ar (SEQ ID NO: 25) (underlined). RAPD-A (SEQ ID NO:21) is the original RAPD fragment amplified by primer OPF-14 (in bold) from *A. actus* (FIG. 10).

FIG. 12. Sequence of the SCAR fragment generated using primers SCAR-Bf (SEQ ID NO:26) and SCAR-Br (SEQ ID NO: 27) (underlined). RAPD-B (SEQ ID NO:22) is the original RAPD fragment amplified by primer OPF-14 (in bold) from *B. multicinctus multicinctus* (FIG. 10).

FIG. 13. Sequence of the SCAR fragments generated using primers SCAR-Zf (SEQ ID NO:28) and SCAR-Zr (SEQ ID NO:29) (underlined), RAPD-Z (SEQ ID NO:23) is the original RAPD fragment amplified by primer OPF-14 (in bold) from *Z. dhumnades* (FIG. 10).

DETAILED DESCRIPTION OF THE INVENTION

Introduction

The present invention provides a method for the authentication of the identity of biological materials based on SCAR (Sequence Characterized Amplified Regions) analysis. SCAR analysis authenticates biological materials by revealing species-specific nucleic acid polymorphisms within chosen organisms. In the invention, SCAR analysis is used to ensure that certain Chinese herbs or other materials in medicinal preparations are not passed off as authentic materials when they are in fact less expensive or less effective substitutes. Because the authentic materials and their substitutes do not share identical DNA sequences, they can be distinguished based on various nucleic acid polymorphisms. These nucleic acid regions that comprise polymorphisms and can be used to identify the different herbs and their adulterants are referred to in this invention as SCAR regions. SCAR regions are regions of known sequence, varying in sequence between species, that can be used to identify or distinguish between a related group of organisms when amplified by PCR or similar techniques. The present invention provides for the authentication of important herbal medicinal materials including *P. ginseng, P .quinquefolius, P. notoginseng* (Burk), *P. japonicus major, P. japonicus, P. trifolius, M.jalapa L.* and *P. acinosa* Roxb, as well as traditional animal materials such as the snakes *Agkistrodon actus, Bungarus multicinctus multicinctus* and *Zaocys dhumnades*.

*Panax ginseng*, commonly referred to as Asian ginseng, is one of the most famous Chinese herbs and it is the most widely recognized plant used in traditional medicine. *Panax ginseng* is native to China, Russia, North Korea, Japan and some areas of North America. *Panax quinquefolius* is related to Asian ginseng and is otherwise known as American ginseng. Like Asian ginseng, American ginseng is used medicinally in order to reduce the effects of stress, improve performance, boost energy levels, enhance memory and stimulate the immune system. Although American and Asian ginseng are related, American ginseng is more expensive and has different applications than its Asian cousin. For example, American ginseng is considered superior for various ailments such as gastrointestinal problems. *Panax notoginseng*, another Chinese herb, is native to China and is grown in the southern and central regions of the country. *P. notoginseng* is commonly used as a remedy for internal and external bleeding. However, this herb has been known to cause miscarriages and must be avoided during pregnancy. *P. japonicus* is Japanese ginseng and *P. trifolius* is dwarf ginseng. Both have similar properties to Asian ginseng yet have different applications. *Mirabilis jalapa L.* and *Phytolacca acinsoa* Roxb are poisonous herbs that have been found to replace *P. ginseng* in some markets.

Figure 1:
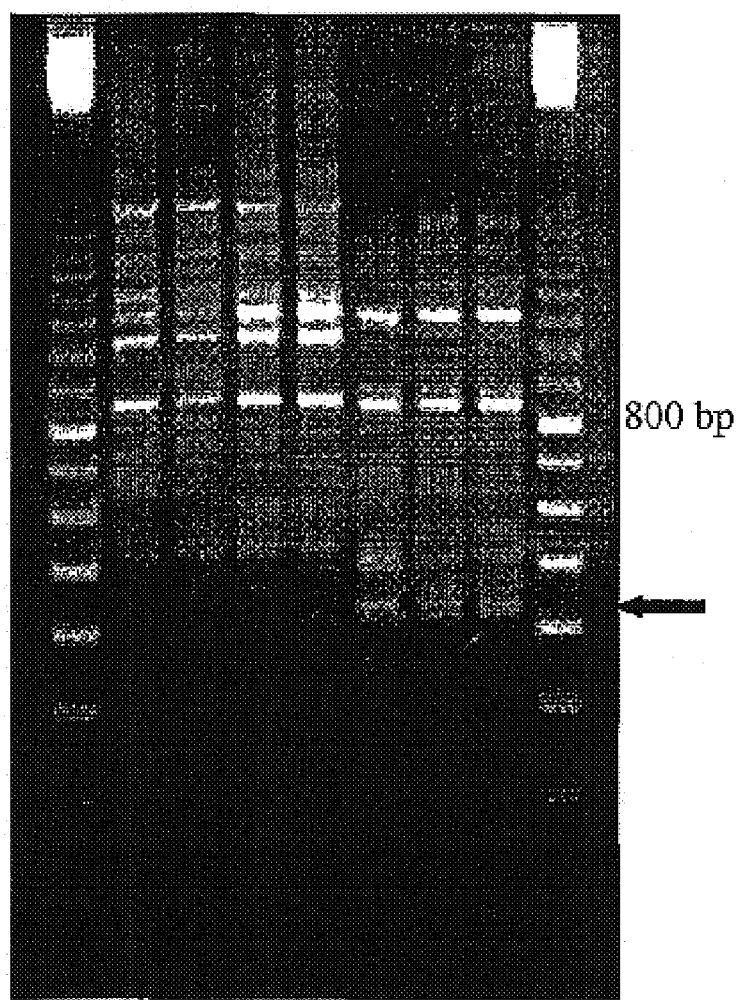
FIG. 1. RAPD analysis of *P. ginseng* and *P. quinquefolius* using the OPC-20 primer (SEQ ID NO: 11). Lanes 1 through 4 are *P. ginseng* from Ji'an of Jilin province, Xingbing of Liaolin province, Kangwon and Kimpo, respectively. Lanes 5 to 7 are *P. quinquefolius* from Canada (samples 5 and 6) and the USA (sample 7), respectively. M is the 100 base pair marker (Phamacia). The arrow indicates the polymorphic band RAPDAG.

Regions polymorphic between these ginseng species and varieties were identified with RAPD, which employs a single random primer to amplify a few discrete regions of the target genome. Amplification with primer OPC-20 identified a band of about 350 bp which varied in size between *P. ginseng* and *P. quinquefolius* (FIG. 1). Sequencing of this band revealed a polymorphic region that was about 25 bp longer in *P. quinquefolius* than in *P. ginseng* (FIG. 2). In addition, several single nucleotide polymorphisms that varied between isolates of each species were also revealed upon sequence comparison (FIG. 2).

Figure 4:
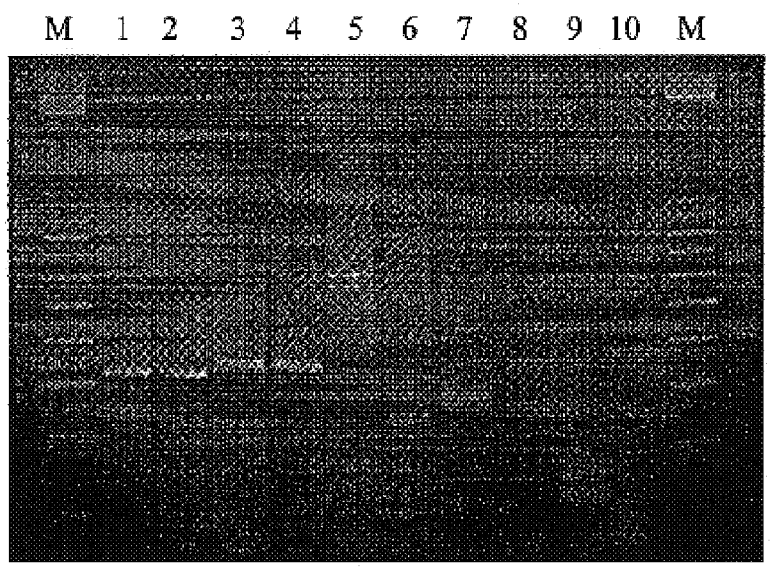
FIG. 4. SCAR analysis of six Panax species and their adulterants using primers SCAR.F1 and SCAR.R1. Lanes 1 and 2 are *P. ginseng* from Ji'an of Jilin province and Kimpo. Lanes 3 and 4 are *P. quinquefolius* from Ontario and Wisconsin. Lane 5 is *P. japonica*. Lane 6 is *P. japonica major*, Lane 7 is *P. trifolius*. Lane 8 is *P. notoginseng*. Lanes 9 and 10 are adulterants *M. jalapa* and *P. acinosa*, respectively.

The sequence of this polymorphic region identified by RAPD was used to design SCAR primers SCAR.F1, SCAR.R1, SCAR.F2, and SCAR.R2, which flank the polymorphic region designated SCAR2 (FIG. 2). Amplification with the pair SCAR.F1 and SCAR.R1 (FIG. 3A), or SCAR.F2 and SCAR.R2 (FIG. 3B) yielded a single diagnostic SCAR band which could be used to distinguish between samples of *P. ginseng* and *P. quinquefolius*, regardless of their area of origin (FIG. 3). Amplification with the SCAR primers SCAR.F1 and SCAR.F2 could also be used to distinguish between other *Panax* species and adulterants commonly found in herbal preparations (FIG. 4).

Figure 5:
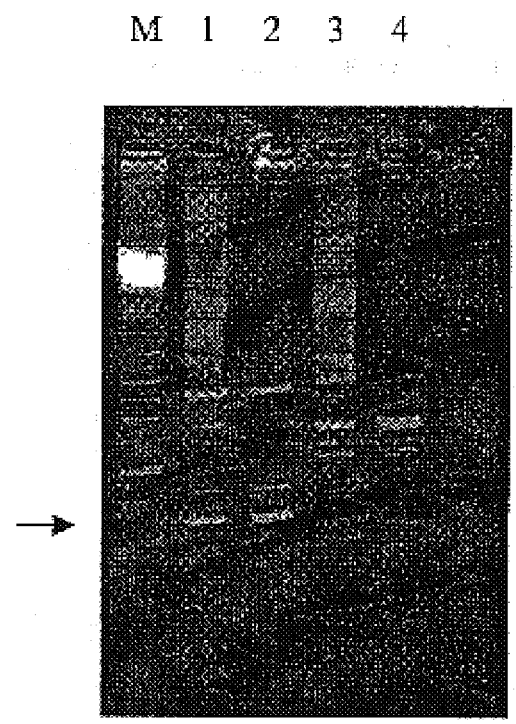
FIG. 5. RAPD analysis of *P. ginseng* and *P. quinquefolius* using the OPC-02 primer (SEQ ID NO: 1). Lanes 1 and 2 are *P. quinquefolius* from USA and Canada, respectively. Lanes 3 and 4 are *P. ginseng* from China. M is the 100 base pair marker (Phamacia). The arrow indicates the polymorphic band C2S8.4 of *P. quinquefolius*.
Figure 9:
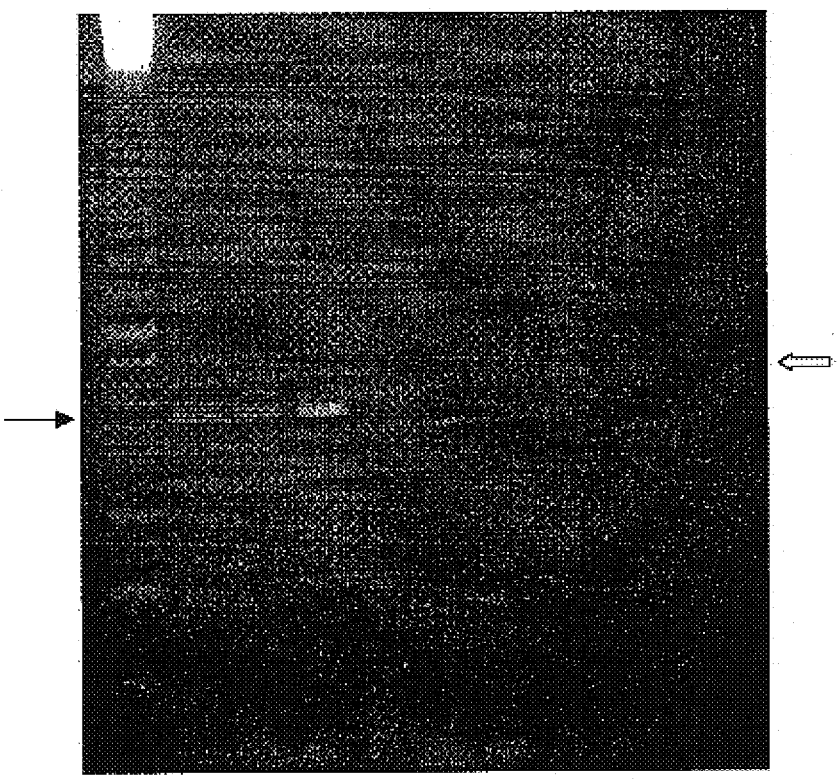
FIG. 9. Simultaneous multiple SCAR analysis with the combined primer set DALP1.7F3, DALP1.7R3, C2S8.4F and C2S8.4R. Lanes 1 to 4 are *P. quinquefolius* from USA and Canada. Lanes.5 to 8 are *P. ginseng* from China. The closed arrow indicates the C2S8.4 band of *P. quinquefolius* and the open arrow indicates the DALP1.7 band of *P. ginseng*.

RAPD analysis may also be used to identify SCAR regions that are amplified only in a particular ginseng species. Thus, FIG. 5 shows a RAPD analysis with primer OPC-02 that identifies a band (C2S8.4) amplified only in *P. quinquefolius*. Sequencing of this band (FIG. 6) yielded SCAR primers C2S8.4F and C2S8.4R which could be used to amplify a single band characteristic of *P. quinquefolius* (FIG. 9).

Polymorphic regions were also identified by DALP, which employs two arbitrary primers rather than one. Amplification with the primers DALP001 and DALPR1 identified a band of about 650 bp present only when DNA from *P. ginseng* was amplified (FIG. 7) The sequence of this band (FIG. 8) was used to design the primers DALP1.7F3 and DALP1.7R3, which amplify a single band characteristic of *P. ginseng*.

Figure 10:
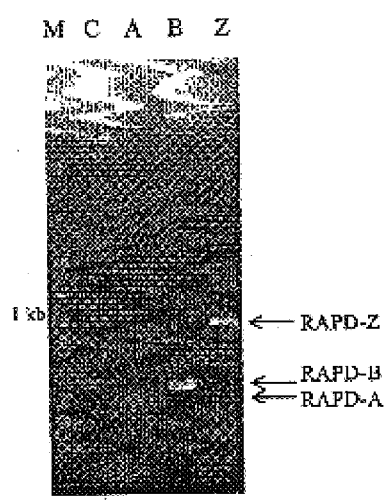
FIG. 10. RAPD analysis of a) *A. arias*, b) *B. multicinctus multicinctus* and z) *Z. dhumnades* using the OPF14 primer (SEQ ID NO:20). The arrows indicate the species-specific RAPD bands. C is the negative control and M is the 100 base pair marker (Pharmacia).
Figure 14:
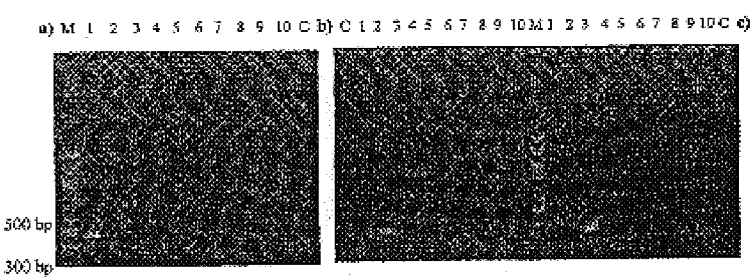
FIG. 14. SCAR analysis using primer: a) SCAR-Af and SCAR-Ar; b) SCAR-Bf and SCAR-Br; c) SCAR-Zf and SCAR-Zr. Lanes 1 to 3 are *A. actus, B. multicinictus multicinictus* and *Z. dhumnades*, respectively. Lanes 4–10 are fish, chicken, duck, cattle, goat, human and pig, respectively. C is the negative control and M is the 100-bp marker from Pharmacia.

Polymorphic bands that distinguished between the snake species *A. actus, B. multicinctus multicinctus*, and *Z. dhumandes* were generated by RAPD analysis with primer OPF-14 (FIG. 10). These bands were sequenced to yield SCAR sequences defined by primer pairs SCAR-Af and SCAR-Ar (FIG. 11), SCAR-Bf and SCAR-Br (FIG. 12), and SCAR-Zf and SCAR-Zr (FIG. 13). Amplification with these primer sets yielded SCAR bands specific to each species of snake, that were amplified neither with DNA from other snakes, nor with DNA from humans or common domestic animals (FIG. 14).

Advantages of the Invention

The method of authentication of Panax species and other materials described herein is suitable for authentication of other traditional Chinese medicinal materials as well. In comparison to the existing procedures of authentication of traditional Chinese medicines, this invention provides the following advantages:

(a) the authentication results are reliable, reproducible and are not affected by the physical forms and ages of the medicinal materials;

(b) it is a method of high sensitivity: a nanogram or less of DNA sample is sufficient;

(c) the SCAR detection method is more specific than other DNA fingerprinting methods using arbitrarily-chosen primers;

(d) the interpretation of the results is straightforward because one only has to analyze the SCAR band for polymorphisms.

Definitions

A "polymorphic region" is a segment of a plant or animal genome that, upon amplification by technqiues such as PCR, varies in length between closely related plant or animal species, or whose presence or absence is characteristic of a plant or animal species. A polymorphic region can be amplified by any suitable oligonucleotide primer set that either reveals a sequence length polymorphism between two or more species of interest, or reveals the presence or absence of an amplification product in a particular species of interest.

A "SCAR," or Sequence Charachterized Amplified Region(s), is an example of a polymorphic region of known sequence. For analysis of specific SCAR sequences, as disclosed herein, primers for amplification may be located at any suitable position within or flanking the SCAR that will identify the polymorphism in question, using methods known to those of skill in the art.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081(1991)); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

In the context of nucleic acid amplification reactions, "high stringency" and "low stringency" conditions generally refer to the temperature maintained during the primer annealing phase of the of the amplification cycle. A temperature of about 36° C. is typical for low stringency amplification as performed in RAPD, although annealing temperatures may vary between about 32° C. and 48° C. depending on primer length. For high stringency amplification, such as amplification of specific SCAR, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec -2 min., an annealing phase lasting 30 sec. -2 min., and an extension phase of about 72° C. for 1–2 min. Extensive discussion of cycling conditions suitable for various amplification techniques may be found in Micheli and Bova, supra.

"Biological sample" as used herein is a sample of a biological tissue or fluid Biological samples include samples obtained from pure sources, extracts, and mixtures, and samples from fresh tissues or fluids as well as dried, prepared, preserved, or processed materials. Biological samples may also include sections of tissues such as frozen sections taken for histologic purposes. A biological sample is typically obtained from a eukaryotic organism, e.g. eukaryotes such as fungi, plants, preferably medicinal plants and herbs, insects, protozoa, birds, fish, reptiles, preferably snakes, and mammals.

General Recombinant Nucleic Acid Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al. eds., *Current Protocols in Molecular Biology* (1994).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonuctcotides is by either native acrylamide gel electrophoresis or by anion-exchange HPLC as described in Pearson & Reanier, *J. Chrom.* 255:137–149 (1983). The sequence of the cloned genes and synthetic oligonucleotides can be verified after cloning using, e.g., the chain termination method for sequencing double-stranded templates of Wallace et a., *Gene* 16:21–26 (1981).

Isolation of Nucleic Acids

Herbal and medicinal materials of all kinds are appropriate sources of nucleic acids for practice of the invention. For the initial identification of polymorphic regions with arbitrary primers, pure samples of the reference herbal or medicinal material are preferred. Once polymorphic regions have been identified and appropriate specific primers to amplify the polymorphic region have been designed, any herbal or medicinal material containing nucleic acids suitable for amplification provides the starting material for practice of the invention.

Methods for isolation of DNA and RNA from biological samples are well known in the art. For example, Micheli and Bova, supra, describe techniques for isolation of nucleic acids from plant and animal sources, including extraction with cationic detergents such as CTAB (hexadecyltrimethylammonium bromide) followed by extraction with organic solvents. Additionally, nucleic acids may be isolated from plant sources by precipitation with potassium acetate, as described in Example I, or from animal sources by proteinase K digestion followed by organic extraction, as described in Example II.

Generation of Polymorphic Amplification Products

Polymorphic regions initially may be identified by any technique that generates a pattern of nucleic acids that is characteristic of the organism. DNA fingerprinting methods, which produce characteristic patterns of DNA amplification products from a sample of an organism's nucleic acids, are preferred. Any fingerprinting method that generates amplification products differing in size between samples of interest, or amplification products present in one sample but absent in another, is suitable for practicing the invention. Particularly preferred are fingerprinting methods based on amplification with arbitrary primers, since no previous knowledge of the target genome is required. Thus, techniques such as RAPD (random amplified polymorphic DNA) (Williams et al., supra), DALP (direct amplification of length polymorphisms) (Desmarais et al., supra), AP-PCR (arbitrarily primed PCR) (Welsh and McClelland, *Nucleic Acids Res.* 18:7213–8 (1990)), AFLP (amplified-fragment length polymorphism analysis) (Savelkoul et al., *J. Clin. Microbiol.* 37(10):3083–91 (1999)) and other methods known in the art can all yield polymorphic regions suitable for use with the invention.

Polymorphic regions may be identified by amplification with a single arbitrary primer, as in the RAPD analysis of Example III, or with two or more arbitrary primers, as in the DALP analysis of Example IV. In general, the choice of fingerprinting technique will depend on the complexity of the fingerprint pattern desired. Techniques that generate complex fingerprints will identify more polymorphisms with fewer primers, and are preferred for distinguishing between closely related organisms. For more distantly related organisms, techniques yielding simpler fingerprints and fewer amplification products are preferred. (See Savelkoul et al., supra).

Basic techniques for nucleic acid amplification may be found in U.S. Pat. Nos. 4,683,195 and 4,683,202; and *PCR Protocols: A Guide to Methods and Applications* (Innis et al. eds. (1990)). Polymorphic regions may be amplified from either DNA or RNA samples, using methods known in the art. Methods such as the polymerase chain reaction (PCR) and ligase chain reaction (LCR) can be used to amplify polymorphic regions directly from genomic DNA, from mRNA, from cDNA, from genomic libraries or cDNA libraries. Degenerate oligonucleotides can be designed to amplify polymorphic regions using the sequences provided herein. Restriction endonuclease sites can be incorporated into the primers. Polymerase chain reaction or other in vitro amplification methods may also be useful, for example, to make nucleic acids to use as probes for detecting polymorphic regions, for nucleic acid sequencing, or for other purposes. Polymorphic regions amplified by PCR or other techniques can be purified from gels and cloned into an appropriate vector.

Analysis of Amplification Products

Resolution of the amplification products is typically by gel electrophoresis, although other methods known in the art such as capillary electrophoresis, mass spectrometry, and chromatographic separation may also be used to analyze the amplification products. Techniques suitable for resolving polymorphic amplification products are well known in the art, including agarose gel electrophoresis, polyacrylamide gel electrophoresis. denaturing gradient gel electrophoresis, and temperature sweep gel electrophoresis. Alternatively, immobilized oligonucleotide arrays may be used to discriminate between polymorphic markers through multiple pairwise comparisons (see U.S. Pat. No. 5,858,659).

The amplification products may be visualized by methods known in the art, such as ethidium bromide staining, silver staining, and incorporation of chemically or radioactively labeled substrates. The method of resolution and visualization will depend on the particular fingerprinting technique used. For example, RAPD analysis employs agarose gel electrophoresis and ethidium bromide staining to visualize the amplification products (see Example III), while DALP analysis employs denaturing polyacrylamide gel electrophoresis and visualizes labeled amplification products by autoradiography (see Example IV). Automated sequencing equipment using fluorescently labeled nucleotides is also suitable for practicing the invention.

Identification of Polymorphic Regions

Figure 7:
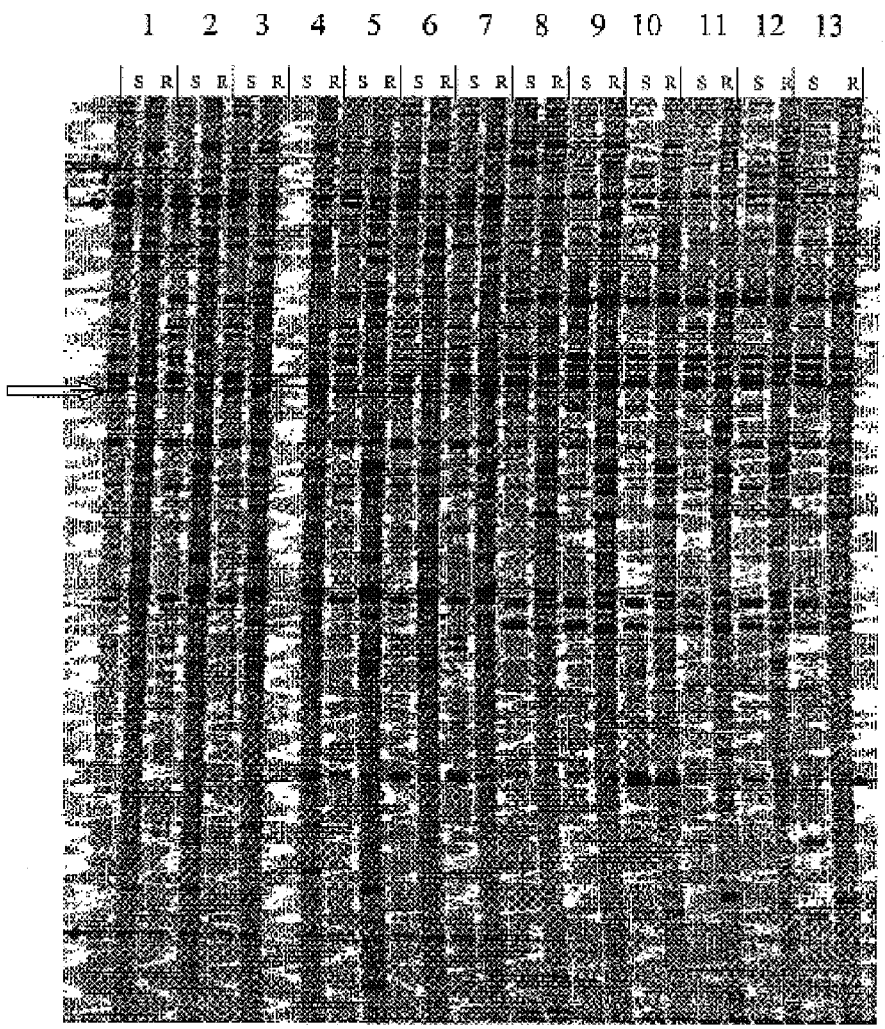
FIG. 7. Acrylamide gel electrophoresis of ginseng genomic DNA amplified with primers DALP001 (SEQ ID NO:15) and DALPR1 (SEQ ID NO:16). Lanes 1 to 7 are *P. ginseng* from Jilin province Ji'an county, Liaolin province Xingbing County, Kangwon, Pochon, Kanghwa, Kumsan and Kimpo respectively. Lanes 8 to 10 are *P. quinquefolius* from different farms of British Columbia, lanes 11 to 13 are from Ontario, a farm in America and Wisconsin, respectively. The open arrow indicates the polymorphic band of *P. ginseng*.

Polymorphic regions suitable for conversion to SCAR appear in the fingerprinting pattern as amplification products characteristic of the species or variety of interest. These may be amplification products that vary in size between the species of interest, or amplification products present only in the species of interest. For example, the SCAR2 polymorphic region appears as an amplification product in the RAPD fingerprint of both $P.$ $ginseng$ and $P.$ $quinquefolius$ (FIG. 1), but is 25 bp longer when amplified from $P.$ $quinquefolius$. In other instances, fingerprinting will reveal amplification products present in only one of the species under analysis. Thus, the C2S8.4 region appears as an amplification product in the RAPD fingerprint of $P.$ $quiniquefolius$ only (FIG. 5), while the DALP1.7 region appears as an amplification product in the DALP fingerprint of $P.$ $ginseng$ only (FIG. 7). It is unnecessary to determine why a particular amplification product fails to appear in one of the species under analysis, so long as the amplification product may be recovered and sequenced from the species in which it does appear.

Marker Isolation and Characterization

Once a polymorphic region is identified from fingerprint analysis, the amplification product is isolated, recovered, and sequenced for conversion into a SCAR. Criteria and methodology for the selection of amplification products are described in Micheli and Bova, supra, at chapters XVII–XIX. In general, amplification products that appear reproducibly, stain intensely, and are well-resolved from other amplification products are most preferred for conversion into SCAR. However, the invention may be practiced with any polymorphic region identified by fingerprinting or other means, so long as it ultimately yields a discrete and characteristic amplification product when amplified as a SCAR with a unique primer set.

Methods for the recovery, cloning, and sequencing of amplification products are well known in the art. See Micheli and Bova, supra, at chapters XVII–XIX. The means by which amplification products are resolved and visualized will dictate the choice of recovery methods. Some fingerprinting methods yield abundant amplification products that may be cloned directly from the fingerprinting gel. For instance, in Example III, the polymorphic regions identified by RAP) analysis were recovered from an agarose gel and cloned directly into a suitable vector. Where the amplification products are less abundant, re-amplification of the isolated polymorphic region provides the substrate for cloning. Thus, in Example IV, the polymorphic band identified by DALP analysis was excised and eluted from the dried sequencing gel, then re-amplified with the original DALP primer pairs before cloning and sequencing by conventional methods.

SCAR Analysis

The sequence of a polymorphic marker provides the information necessary to convert the marker into a SCAR. Conversion of a marker to a SCAR is accomplished by designing oligonucleotide primers that will specifically amplify the polymorphic region from a test sample. Such primers may be designed by simply extending the short arbitrary fingerprinting primers into longer and more specific primers. For example, SCAR.F2 and SCAR.R2, primers flanking the SCAR2 polymorphic region of $P.$ $ginseng$ and $P.$ $quinquefolius$, were designed by extending the 3' end of the RAPD primer into the sequence of SCAR2 (FIG. 2). These additional nucleotides allow amplification of a single SCAR band under stringent conditions (FIG. 3B). However, the specific primers for SCAR amplification need not be related to the primers used initially to identify the polymorphic region. Amplification with any primer set within the SCAR sequence, chosen according to methods well known in the art, is suitable to practice the invention so long as it preserves the amplification pattern characterizing the species of interest. Thus, in one embodiment of the invention, the SCAR2 polymorphic region is amplified with primers SCAR.F1 and SCAR.R1, internal to the RAPD primer binding sites, and the chosen primers have no sequence similarity to the RAPD primer (FIG. 2). Amplification with either primer pair demonstrates the 25 bp shift in SCAR2 that differentiates between $P.$ $ginseng$ and $P.$ $quiquefolius$ (FIG. 3).

SCAR generated from polymorphic regions that differ in size between species permit sample identification based on SCAR size shifts. In this embodiment of the invention, an unknown sample may be identified by comparing the size of the amplified SCAR region from the unknown sample and the amplified SCAR region from a reference sample (e.g., FIG. 3). Where the SCAR are present only in one particular species of interest, rather than varying in size between species, an unknown sample may be identified by amplifying nucleic acid from the unknown sample with the chosen SCAR primers and scoring for the presence or absence of the expected SCAR amplification product (e.g., FIG. 14).

Multiple SCAR may be simultaneously analyzed by combining primer sets in a single amplification reaction. Practicing the invention in this embodiment is especially useful to identify an unknown sample as one of several possible known species, each species being characterized by the presence of a SCAR absent from the others. Such an analysis is illustrated by Example VI, in which sample nucleic acids are amplified with the combined primer set of DALP1.7F3, DALP1.7R3, C2S8.4F, and C2S8.4R. Whether the $P.$ $ginseng$-specific SCAR DALP1.7 or the $P.$ $quiquefolius$-specific SCAR C2S8.4 is amplified identifies the sample as $P.$ $ginseng$ or $P.$ $quiquefolius$.

Sequence information from a polymorphic region may also be used in other assays that discriminate between polymorhic nucleic acids, such as allele-specific PCR (Wu et al., *Proc. Natl. Acad. Sci. USA*86:2757–60 (1989)) and allele-specific ligation (Landegren et al., *Science*241:1077–80 (1988)).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The following examples are provided by way of illustration only and not by way of limitation. Those of skill in the art will readily recognize a variety of noncritical parameters that could be changed or modified to yield essentially similar results

EXAMPLE I

Extraction of Plant DNA

Dried or fresh roots of *Panax* species were obtained from the following sources: *P. ginseng* samples were from China (Ji'an county of Jilin province, Xingbing county and Xinkiahe county of Liaolin province and Korea (Kangwon, Pochon, Kanghwa, Kumsan and Kimpo); *P. quinquefolius* samples were from farms in Ontario, British Columbia and Wisconsin. *P. notoginseng* (Burk) and *P. japonicus major* were from China, *P. japonicus* was from Japan and *P. trifolius* from the USA. Adulterants *M. jalapa L.* and *P. acinosa* Roxb were from Hong Kong. All ginseng plants were identified and deposited at the Institute of Chinese Medicine of the Chinese University: The samples were rinsed with 70% ethanol and then distilled water to remove any surface contaminants. The samples were ground into fine powder in liquid nitrogen using a mortar and pestle. Ground sample powder was added into 15 ml of DNA extraction buffer (100 mM Tris-HCl pH 8.0, 50 mM EDTA pH 8.0, 500 mM NaCl, 10 mM 2-mercaptoethanol) and 2 ml of 10% SDS. The tube was incubated at 65° C. for 12 min. 5 ml of 5 M potassium acetate was added and the solution was incubated on ice for 30 mm. The protein/SDS precipitate was pelleted by centrifugation (Sanyo MSE Micro Centaur, San Diego) at 12,000 rpm for 30 min. (4° C.). The supernatant was poured through a siliconized filter funnel, packed with polypropylene wool, into a clean centrifuge tube. 15 ml of isopropanol (−20° C.) was added and the mixture was incubated at −20° for 30 min. The nucleic acids were pelleted at 4° C. by centrifugation at 8,000 rpm for 20 20 min. The supernatant was poured off and the pellet was allowed to partially dry by inverting the tube. The nucleic acids were gently redissolved in 700 µl of Tris/EDTA buffer (50 mM Tris-HCl pH 8.0, 10 mM EDTA pH 8.0). They were then transferred to an Eppendorf tube and spun for 5 min to remove insoluble contaminants. The supernatant was transferred to a new Eppendorf tube and mixed with 75 µl of 3 M sodium acetate and 500 µl of cold (−20° C.) isopropanol, and examined for a fibrous nucleic acid precipitate. The nucleic acids were pelleted for 30 sec and the supernatant was carefully poured off. The pellet was washed with 80% ethanol (1 ml. 2×), vacuum-dried and redissolved in 80µl of water. Further purification by CsCl gradient ultracentrifugation is optional.

EXAMPLE II

Extraction of Animal DNA

Dried or fresh animal samples were obtained from the following sources: *A. actus, B. multicinctus multicinctus, Z. dhumnades* were from Hong Kong. Other common poultry and livestock, e.g. fish, chicken, duck, cattle, goat and pig were from markets in Hong Kong. A human blood sample was from a normal Chinese. Nucleated cells in the human blood were first isolated. 30 ml water was mixed with 10 ml blood quickly and 10×PBS was added to give 1×PBS concentration in the blood mixture. It was centrifuged at 400×g for 5 min. and washed with 1×PBS. It was centrifuged again and the supernatant was then removed. The samples, except blood, were pulverized using an acid-washed pestle and mortar filled with liquid nitrogen. 0.5 ml RSB buffer (25 mM EDTA, 10 mM NaCl, 10 mM Tris-Cl, pH 7.4) and 50 µl 10% SDS were added to these fine powders as well as the blood pellet. The mixture was gently inverted and 0.1 ml proteinase K (10 mg/ml) was added. It was incubated at 65° C. for 2 hr. 70 µl 5 M NaCl was then added and the solution was extracted with 0.7 ml salt-saturated phenol/chloroform/isoamyl alcohol (25:24:1). The solution was mixed by repeated inversion and centrifuged at 2500×g for 10 min. to separate phases. The upper aqueous phase was transferred to a fresh tube and extracted with chloroform/isoamyl alcohol (24:1). 2 ml absolute ethanol was added to the aqueous phase to precipitate DNA. After incubation at −20° C. for 30 min., the mixture was centrifuged at 14,000 rpm 20 for min, and the supernatant was removed. The DNA pellet was washed with 70% ethanol and allowed to dry 30 min. The sample DNA was dissolved in 50µl water.

EXAMPLE III

Identification of Polymorphic Regions by RAPD Fingerprinting

Plant genomic DNA was amplified using the primers: OPC-02, OPC-20 or OPF-14 (Operon, Alameda).

| | |
|---|---|
| OPC-02: | GTGAG GCGTC (SEQ ID NO:1) |
| OPC-20: | ACTTC GCCAC (SEQ ID NO:11) |
| OPF-14: | TGCTG CAGGT (SEQ ID NO:20) |

RAPD was performed in a 25 µl solution containing 10–25 ng plant DNA, 0.1 mM dNTPs, 0.2 µM OPC-20 primer (Operon, Alameda), 1×Taq buffer (10 mM Tris-HCl, pH 8.3; 50 mM KCl; 0.001% gelatin), and 0.5 U of Taq polymerase. The reaction took place in a Thermolyne thermocycler through 45 cycles of 94° C., 1 min.; 36° C., 2 min; 72° C., 2 min. The PCR products were resolved by a 1.5% TBE gel.

Desirable RAPD polymorphic bands were excised from the gel and purified using the GENECLEAN kit (BIO 101, Vista) or Microspin SR-300 columns (Pharmacia, Buckinghamshire). The PCR product was filled in at the 3' end and cloned into XmaI/BAP blunt-ended pUC 19 (Pharmacia, Buckinghamshire). Both strands of the fragment were sequenced by a T7 sequencing kit (Pharmacia, Buckinghamshire). The sequencing procedure was done according to the manufacturer's instructions. Sequences of the primers used for PCR are denoted in FIG. 2.

EXAMPLE IV

Identification of Polymorphic Regions by DALP Fingerprinting

Primers DALP0001 and DALPR1 were labeled in a final volume of 20 µl containing 50 pmoles primer, 1 µl $^{33}$P-ATP (3 μCi/mmole, 10 mCi/ml), 10U T4polynucleotide kinase and 1×T4 polynucleotide kinase. The reaction was incubated at 37° C. for 30 minutes to one hour and the kinase was inactivated at 70° C. for 5 min. at the end of the reaction.

| DALP001: | GTTTT CCCAG TCACG ACGC (SEQ ID NO:15) |
|---|---|
| DALPR1: | AACAG CTATG ACCAT GA (SEQ ID NO:16) |

For amplification with labeled DALP001 primer, 20 μl reaction solution contained 50–100 ng plant genomic DNA, 2.5 pmoles of labeled DALP001 primer, 7.5 pmoles of unlabeled DALPR1 primer, 100 μM dNTPs, 1.75 mM MgCl$_2$, 1×Taq buffer and 0.5 U Taq DNA polymerase. For the DALPR1 primer-labeled amplification reaction, 20 μl reaction solution contained 50–100 ng plant genomic DNA, 2.5 pmoles of unlabeled DALP001 primer, 7.5 pmoles of labeled DALPR1 primer, 100 μM dNTPs, 1.9 mM MgCl$_2$, 1×Taq buffer and 0.5 U Taq DNA polymerase. PCR amplification was performed in a MJ PTC-100™ thermal controller using the following cycling profile: 95° C. 2 min.; 34 cycles of 91° C. 30 sec, 55° C. 30 sec and 72° C. for 1 min.

Following denaturing polyacrylamide gel electrophoresis and autoradiography of the reaction products, DNA from the polymorphic DALP band was eluted from the dried sequencing gel. One μl of the supernatant was used as the template in a PCR re-amplification in a final volume of 20 μl containing 10 μM original primer pairs, 100 μM. dNTPs, 4 mM MgCl$_2$, 1×Taq buffer and 0.5 U Taq DNA polymerase. PCR amplification was performed using the cycling profile of 95° C. 2 min; 34 cycles of 91° C. 30 sec, 55° C. 30 sec and 72° C. for 1 min. The re-amplified products were electrophoresed on a 1.5% agarose gel and purified from the gel using the BIO 101 GENECLEAN III kit.

To sequence the re-amplified polymorphic band, the 3' hydroxyl termini of the purified DALP fragments were modified. Twenty-five ng of modified DALP products were ligated to 100 ng Xma I/BAP pUC 18 vector. Both strands of the fragment were sequenced by a T7 sequencing kit (Pharmacia, Buckinghamshire). The sequencing procedure was done according to the manufacturer's instructions. Sequences of the primers used for PCR are denoted in FIG. 8.

EXAMPLE V

Scar Analysis of Herbal and Medicinal Materials

The sample genomic DNA was amplified using pairs of SCAR primers SCAR.F1 and SCAR.R1, SCAR.F2 and SCAR.R2, SCAR-Af and SCAR-Ar, SCAR-Bf and SCAR-Br, SCAR-Zf and SCAR-Zr:

| SCAR.F1: | CAAGT CAACT GCAGG GGTTA AGAA (SEQ ID NO:7) |
|---|---|
| SCAR.R1: | CCCTT TTATT TGAAC TATCT TTCTC TCTC (SEQ ID NO:8) |
| SCAR.F2: | TTCGC CACCC GGAGC AGCAT TG (SEQ ID NO:9) |
| SCAR.R2: | TTCGC CACAA TAACT ATGTG ATGGA AC (SEQ ID NO:10) |
| SCAR-Af: | AGCCT GATTA TTCAA GTTGG (SEQ ID NO:24) |
| SCAR-Ar: | GGAAT GAATT TGAAG GGAGA (SEQ ID NO:25) |
| SCAR-Bf: | CAATG AAAGG GAAGG TTGGT (SEQ ID NO:26) |
| SCAR-Br: | GGAAT TTGCT CTGCA ATTTG (SEQ ID NO:27) |
| SCAR-Zf | AAAGG TCCCA AGACA ACTTA (SEQ ID NO:28) |
| SCAR-Zr: | GCTAG TCCAT TTCCC GTTTC (SEQ ID NO:29) |

SCAR were amplified in a 25 μl volume containing 40 ng genomic DNA. 1×Taq buffer, 0.1 mM dNTPs, 2 mM MgCl$_2$ 1 μM of each primer and 1 unit of Taq DNA polymerase. The cycling profile used was: 40 cycles of 91° C. 1 min; 60° C. (for primers SCAR.F2 and SCAR.R2), or 50° C. (for the other SCAR primers) 1 min; and 72° C. for 1.5 min. After the reaction, the products were resolved by 2% TBE agarose gels (FIGS. 3, 4, and 14).

EXAMPLE VI

Multiple Simultaneous Scar Analysis with Combined Primer Sets

Sample plant genomic DNA was amplified using the two pairs of SCAR primers C2S8.4F and C2S8.4R, DALP1.7F3 and DALP1.7R3:

| C2S8.4F: | GTGAG GCGTC TAAAC AAAAA CGAAG (SEQ ID NO:13) |
|---|---|
| C2S8.4R: | GTGAG GCGTC AAGTA AGAAT GGTC (SEQ ID NO:14) |
| DALP1.7F3 | GCGTC CCACT GACCC TTTTG TACA (SEQ ID NO:18) |
| DALP1.7R3 | ACAGC TATGA CCATG ATGCA ACATC (SEQ ID NO:19) |

PCR was hot-started in a 50 μl volume containing 40 ng plant DNA, 1×Taq buffer, 1 mM dNTPS, 4 mM MgCl$_2$, 50μM of C2S8.4 primers, 40 μM of DALP1.7 primers and 5 unit of Taq DNA polymerase. The cycling profile used was: 30 cycles of 91° C. 1 min; 58° C. 1 min; and 72° C. for 2 min. After the reaction, the products were resolved by a 2.5% TBE agarose gel (FIG. 9).

What is claimed is:

1. A method for determining whether a given herbal material is that of *Panax gingseng, Panax quinquefolius, Panax notoginseng* (Burk), *Panax japonicus major, Panax japonicus, Panax trifolius, Mirabilis jalapa* L., or *Panax acinosa Roxb*, the method comprising the steps of:

(i) extracting nucleic acid from the herbal material;

(ii) amplifying a polymorphic region of the extracted nucleic acid using at least two different oligonucleotide primers that flank the polymorphic region;

(iii) resolving amplified products according to their size;

(iv) detecting the amplified products; and (v) comparing the amplified products with known amplification products of herbal material, thereby determining whether the herbal material is that of *Panax gingseng, Panax quinquefolius, Panax notoginseng* (Burk), *Panax japonicus major, Panax japonicus, Panax trifolius, Mirabilis jalapa* L., or *Panax acinosa Roxb*, or whether the herbal material is from another source, wherein the extracted nucleic acid comprises a nucleic acid selected from the group consisting of SEQ ID NO: 2.

2. The method of claim 1, wherein the extracted nucleic acid is genomic DNA.

3. The method of claim 1, wherein the sizes of the detected amplification products are compared with known sizes of amplification products from known herbal material to identify the herbal material.

4. The method of claim 1, wherein the presence of an amplification product is detected to identify the herbal material.

5. The method of claim 1, wherein the absence of an amplification product is detected to identify the herbal material.

6. A method for determining whether a given herbal material is that of *Panax gingseng, Panax quinquefolius, Panax notoginseng* (Burk), *Panax japonicus major, Panax japonicus, Panax trifolius, Mirabilis jalapa* L., or *Panax acinosa Roxb*, the method comprising the steps of:

(i) extracting nucleic acid from the herbal material;

(ii) amplifying a polymorphic region of the extracted nucleic acid using at least two different oligonucleotide primers that flank the polymorphic region;

(iii) resolving amplified products according to their size;

(iv) detecting the amplified products; and (v) comparing the amplified products with known amplification products of herbal material, thereby determining whether the herbal material is that of *Panax gingseng, Panax quinquefolius, Panax notoginseng* (Burk), *Panax japonicus major, Panax japonicus, Panax trifolius, Mirabilis jalapa L.*, or *Panax acinosa Roxb*, or whether the herbal material is from another source, wherein the nucleic acid is amplified with a primer set selected from the group consisting of SEQ ID NO: 7, SEQ ID NO: 8.

7. The method of claim 1, wherein the herbal material is that of *Panax quinquefolius* or *Panax gingseng.*

8. The method of claim 1, wherein the *Panax quinquefolius* is from the United States or Canada.

9. The method of claim 1, wherein the *Panax quinquefolius* is from the Wisconsin, British Colombia, or Ontario.

10. The method of claim 6, wherein the extracted nucleic acid is genomic DNA.

11. The method of claim 6, wherein the sizes of the detected amplification products are compared with known sizes of amplification products from known herbal material to identify the herbal material.

12. The method of claim 6, wherein the presence of an amplification product is detected to identify the herbal material.

13. The method of claim 6, wherein the absences of an amplification product is detected to identify the herbal material.

14. The method of claim 6, wherein the herbal material is that of *Panax quinquefolius* or *Panax gingseng.*

15. The method of claim 6, wherein the *Panax quinquefolius* is from the United States or Canada.

16. The method of claim 6, wherein the *Panax quinquefolius* is from Wisconsin, British Colombia, or Ontario.

* * * * *

SEQUENCE LISTING

<160> NUMBER OF SEQ ID NOS: 29

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:primer OPC-02

-continued

<400> SEQUENCE: 1
gtgaggcgtc                                                                                  10

<210> SEQ ID NO 2
<211> LENGTH: 419
<212> TYPE: DNA
<213> ORGANISM: Panax quinquefolius
<220> FEATURE:
<223> OTHER INFORMATION: RAPDAG original RAPD fragment amplified by
      primer OPC-20 from farm in USA

<400> SEQUENCE: 2
ttcgccaccc ggagcagcat tgagatccgc caagtcaact gcaggggtta agaagcccttt       60 aaaaatccag tgaagtttcc ttggtctgct tcattgcttc tcaattcgat catccggtgtg     120 agctcgtcaa ccttttgtca gtcaaagtcc tcacccactc ctgcccattg aaaattccac      180
cttccccgcc cattgaaaat tttgccaact tatttaatac acttctcctt ccattcggct      240
ataaaggcag ctaagcataa ggatcaaata caccagcaac aatacgtact cccatcctag      300
agaggaaaag agaagggag agaaaagctt ttgtaaagct ttagaaaaat agagagagaa        360
agatagttca aataaaaggg tgttttattt gggttccatc acatagttat tgtggcgaa        419

<210> SEQ ID NO 3
<211> LENGTH: 350
<212> TYPE: DNA
<213> ORGANISM: Panax quinquefolius
<220> FEATURE:
<223> OTHER INFORMATION: WAG from Wisconsin

<400> SEQUENCE: 3
caagtcaact gcaggggtta agaagcccttt aaaaatccag tgaagtttcc ttgatctgct       60
tcattgcttc tcaattcgat catccggtgtg agctcgtcaa ccttttgtca gtcaaagtcc     120
tcacccactc ctgcccattg aaaattccac cttccccgcc cattgaaaat tttgccaact      180
tcatttaata cacttctcct tccattcggc tataaaggca gctaagcata aggatcaaat      240
acaccagcaa caatacgtac tcccatccga gagaggaaaa gagaagggag agaaaagctt     300
ttgtaaagct ttagaaaaat agagagagaa agatagttca aataaaaagg                  350

<210> SEQ ID NO 4
<211> LENGTH: 349
<212> TYPE: DNA
<213> ORGANISM: Panax quinquefolius
<220> FEATURE:
<223> OTHER INFORMATION: AG from Ontario

<400> SEQUENCE: 4
caagtcaact gcaggggtta agaagcccttt aaaaatccagt gaagtttcct tgatctgctt      60
cattgcttct caattcgatc atcggtgtga gctcgtcaac cttttgtcag tcaaagtcct      120
cacccactcc tgcccattga aaattccacc ttccccgccc attgaaaatt ttgccaactt      180
catttaatac acttctcctt ccattcggct ataaaggcag ctaagcataa ggatcaaata      240
caccagcaac aatacgtact cccatccgag agaggaaaag agaagggaga gaaaagcttt     300
tgtaaagctt tagaaaaata gagagagaaa gatagttcaa ataaaaagg                    349

<210> SEQ ID NO 5
<211> LENGTH: 325
<212> TYPE: DNA
<213> ORGANISM: Panax ginseng

```
<220> FEATURE:
<223> OTHER INFORMATION: DG from Xingbing of Liaolin province

<400> SEQUENCE: 5
caagtcaact gcaggggtta agaagccctt aaaaatccag tgaagtttcc ttgatctgct      60
tcattacttc tcaattcggt catcggtgtg agctcgtcaa ccttttgtta gtcaaagtcc     120
tcacccactc ccgcacattg aaaattttgc caacttcatt taatacactt ctccttccat     180
tcggctataa aggcagctaa gcataaggat caaatacacc agcaacaata catactccca     240
tccgagagag gaaaagagaa agggagagaa aagcttttgt aaagctttag aaaaatagag     300
agagaaagat agttcaaata aaagg                                           325

<210> SEQ ID NO 6
<211> LENGTH: 325
<212> TYPE: DNA
<213> ORGANISM: Artificial Sequence
<220> FEATURE:
<223> OTHER INFORMATION: HG from Kangwon
<220> FEATURE:
<223> OTHER INFORMATION: Description of Artificial Sequence:primer
      SCAR.F1

<400> SEQUENCE: 6
caagtcaact gcaggggtta agaagccctt aaaaatccag tgaagcttcc ttgatctgct      60
tcattacttc tcaattcggt catcggtgtg agctcgtcaa ccttttgtta gtcaaagtcc     120
tcacccactc ccgcacattg aaaattttgc caacttcatt taatacactt ctccttccat     180
tcggctataa aggcagctaa gcataaggat caaatacacc agcaacaata catactccca     240
tccgagagag gaaaagagaa agggagagaa aagcttttgt aaagctttag aaaaatagag     300
agagaaagat agttcaaata aaagg                                           325

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:SCAR primer
      SCAR.R1

<400> SEQUENCE: 7
caagtcaact gcaggggtta agaa                                             24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:SCAR primer
      SCAR.F1

<400> SEQUENCE: 8
cccttttatt tgaactatct ttctctctc                                        29

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:SCAR primer
      SCAR.F2

<400> SEQUENCE: 9
```
ttcgccaccc ggagcagcat tg                                               22

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:SCAR primer
      SCAR.R2

<400> SEQUENCE: 10
ttcgccacaa taactatgtg atggaac                                          27

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:primer
      OPC-20

<400> SEQUENCE: 11
acttcgccac                                                             10

<210> SEQ ID NO 12
<211> LENGTH: 577
<212> TYPE: DNA
<213> ORGANISM: Panax quinquefolius
<220> FEATURE:
<223> OTHER INFORMATION: polymorphic band fragment generated by OPC-02
      primer

<400> SEQUENCE: 12
gtgaggcgtc taaacaaaaa cgaagaagca gaaagcacag aaccagagac caaagaagaa       60 gaaagaaga aaaaagaaa aagcagagaa cgaaaaaaaa gaaagaaaag aaagcagcgt        120
cgcgactcgc gactagagaa gaaagaagaa catactagca aagaagaagc aatcggagct      180
aggggtagtc gtcattggtc agagttccag tattcaacca ctcaccagtc tctctctccc      240
aaatctcccc tttctactct tctactgtaa atcgcgatta gggccaatta tctcttctcg      300
gaacgacgtc gttttttttt aaaccggttc tccattgggt caatccatac ccatagcaaa      360
tccaaatcgc tctctcagct cgtctaagta gtcgacgagg cgcccatggc gacgacttgc      420
tttcccaggc actcgacttg cagacctcca ccaagtcggc caaccgcctt cttcttcgga      480
tcgactggac gtctagtcga cgcattaaca actatgacac aaactaaggc ttttacaatt      540
agagatgatc aaagaccatt cttacttgac gcctcac                               577

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:SCAR primer
      C2S8.4F

<400> SEQUENCE: 13
gtgaggcgtc taaacaaaaa cgaag                                            25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:SCAR primer

C2S8.4R

<400> SEQUENCE: 14
gtgaggcgtc aagtaagaat ggtc     24

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:DALP primer
      DALP001

<400> SEQUENCE: 15
gttttcccag tcacgacgc     19

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:DALP primer
      DALPRI

<400> SEQUENCE: 16
aacagctatg accatga     17

<210> SEQ ID NO 17
<211> LENGTH: 636
<212> TYPE: DNA
<213> ORGANISM: Panax ginseng
<220> FEATURE:
<223> OTHER INFORMATION: polymorphic band fragment of sample of Jilin
      province, Ji'an County, identical to Kangwon

<400> SEQUENCE: 17
cgctcccact gacccttttg tacacactag gttcattctt attgctgata aaatcaaact     60
cttttgattt atttcatcaa agcgaatgtt ccattttga gaagcttgct tcagtccatt    120
cctctgagtg tctacaactc ttacctcatg taactggatc atcatcttct gtgatgtgta    180
cctcatcatc atcatcatct ataatgaatc catacctcct aggtatcgtc ggtattattc    240
tagatttacg attcggttgt ggtgcaatag gtctatctac aggttcctct tatttgactt    300
atagtgtttt gtggttcttg aactcttcaa gatctattat cctcccacta gccccttaa    360 tgataaacac ctttatctta gaaggtagtg tgtttcacaa taaacacctt ttgctaagta    420
ggattataga gacattgagg tcagccacgt attgccacac ccattctgta ggggtattta    480
cgagcagttt ggtcttgctg tatgtgtggt tcatgtcaca cttgagactg attggcatat    540
tctgacgtca tgggtactat ttttcccatg agatagccat gtcttactct tttcagccag    600
cgtagtgtac agatgttgca tcatggtcat agctgt     636

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:designed
      SCAR primer DALP1.7F3

<400> SEQUENCE: 18
gcgtcccact gacccttttg taca     24

```
<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:designed
      SCAR primer DALP1.7R3

<400> SEQUENCE: 19
acagctatga ccatgatgca acatc                                          25

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence:primer
      OPF-14

<400> SEQUENCE: 20
tgctgcaggt                                                           10

<210> SEQ ID NO 21
<211> LENGTH: 561
<212> TYPE: DNA
<213> ORGANISM: Agkistrodon actus
<220> FEATURE:
<223> OTHER INFORMATION: original RAPD fragment RAPD-A amplified by
      primer OPF-14

<400> SEQUENCE: 21
tgctgcaggt cctgtcagcc tgattattca agttggtgag gtccaagatg agggtctttt    60
ctgctcttac cctctggacc atcttgctcc ccaatgtaag gttgcccccaa ccctcctgtc  120 ttttcgtaag ggcctgaaga cgtggctttg caatgcaaat caaacaaaac accaccattt   180
ggggccccag tgaatgaaca gcacaataga ggtggttgat agagtcataa cagatcccac   240
ctgccctcca atccaccccc caacctcccc atgtgtcttt gattgtaagg tttgatttta   300
acattttgtg ttttaactaa gatgtaacta taagccgcag agagttactc tatggtaaga   360
tgcagggcca ataaatttga taaataaaca aatcaaatca aatcaattgt cactgccttc   420
ttactgatat gcctgctaca tctaagctgc atatttctcc cttcaaattc attccaagtt   480
caaaaatatc tcctacattt tcaaatcaag cagcagcacc atgaggagca atcatcttat   540
aatcagtatt cacctgcagc a                                             561

<210> SEQ ID NO 22
<211> LENGTH: 605
<212> TYPE: DNA
<213> ORGANISM: Bungarus multicinctus
<220> FEATURE:
<223> OTHER INFORMATION: original RAPD fragment RAPD-B amplified by
      primer OPF-14

<400> SEQUENCE: 22
tgctgcaggt cccattagtt aatgagtaac ctcccggggc ccaaaaagag agttttctct    60
gcctttaccc cgctgcccgc cgtgaaaacc tccccactct cttggccttt cataaaggtg   120
ttaaaaacat ggctctgcat cttttcttgc accaatgaaa gggaaggttg gtgccctgac   180
agcctcccac cttttaatca atttgttaca ttccttgctt gttttaaatt ttacatactt   240
ttatatgctt ttaatacttt attgtatttg ctttgaattg ctttgtgaag gagatggaag   300
gttcttaaat atgacaaaca aataattagt gaattcaggt gtgttttgct gtgtagggaa   360
```

```
atggtatact atatgtttag tatattgtat cttccatgca tatcaggtat acaggttgga    420
tctgagcaaa actgagagca aattgggagc aaattcccat ctcttcaact cctttaaaaa    480
cactccggag attaggaaaa cttcatatga agaaggatgt caatagagat catatttctt    540
tttccactgt tttgtttctg agaatgtctc cttggatcag aaaagaaaac tgttgacctg    600
cagca                                                                605
```

```
<210> SEQ ID NO 23
<211> LENGTH: 929
<212> TYPE: DNA
<213> ORGANISM: Zaocys dhumnades
<220> FEATURE:
<223> OTHER INFORMATION: original RAPD fragment RAPD-Z amplified by
      primer OPF-14

<400> SEQUENCE: 23
tgctgcaggt atgatagttc caaaaattac tagccttcaa tttctaaaca acaaattaaa     60
ttctgattac aatatactac tcagtgatat tgttcattaa gaggaattct acatatttaa    120
caattgtatt ctagtgcaat tttgaaatat aaaagctcaa gcaaaacaga ttaagcccct    180
ttcaactcga aaaggtccca agacaactta aagatctac cagtggtttc aaagtaaaaa    240
aaaaacaaaa actaaatagg ttttaggatt tcacaagtaa aagggtgaca atagagcata    300
ccacagttgt ttttggtata attgtagttt taattgtcaa agcaattaaa tgtaactggg    360
cagatgaaag ctgagtggac caataagaac agattgacta cacctcttaa ttaagaagga    420
aagaatgtac atttgtgaat gttgttcact atatatatag agagagaaca aatgaaagga    480
tacgatatca tcaagggagt taaagaattg aaacgggaaa tggactagca agaagaactg    540
atggtaggtg gaccaaggca gccatagact ggatccccct tgataataag tggccttgaa    600
agagacctac agtaaaacaa gactgatcaa taacatcagc aagtattgcg ggccaaaaaa    660
agctcaggac cattggaaac atgaggaaga ggcatcctgc agtggataga caatggctaa    720
gatgatgatg atgatgatga tgatgatgat gatgatgatg atgcagtcaa atatcagtaa    780
atgcagttgc ttcgatatat ggagagtaac aagcaagcaa atgttgcttt tgcttttgac    840
ttgctgtggc acaaacacta aatctaatga ccatacatat tgaaagatgt tagtttgctg    900
tatgaaatga acacttttga cctgcagca                                      929
```

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Af

<400> SEQUENCE: 24
agcctgatta ttcaagttgg                                                 20
```

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Ar

<400> SEQUENCE: 25
ggaatgaatt tgaagggaga                                                 20
```

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Bf

<400> SEQUENCE: 26
caatgaaagg gaaggttggt                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Br

<400> SEQUENCE: 27
ggaatttgct ctgcaatttg                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Zf

<400> SEQUENCE: 28
aaaggtccca agacaactta                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:SCAR primer
      SCAR-Zr

<400> SEQUENCE: 29
gctagtccat ttcccgtttc                                                   20
```